(12) United States Patent
Hayes et al.

(10) Patent No.: US 7,291,710 B2
(45) Date of Patent: Nov. 6, 2007

(54) DETECTION OF SPECTRIN AND SPECTRIN PROTEOLYTIC CLEAVAGE PRODUCTS IN ASSESSING NERVE CELL DAMAGE

(75) Inventors: Ronald L. Hayes, Gainesville, FL (US); Kevin K. W. Wang, Gainesville, FL (US); Brian R. Pike, Derwood, MD (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 488 days.

(21) Appl. No.: 10/660,069

(22) Filed: Sep. 11, 2003

(65) Prior Publication Data

US 2007/0003982 A1 Jan. 4, 2007

Related U.S. Application Data

(60) Provisional application No. 60/409,920, filed on Sep. 11, 2002.

(51) Int. Cl.
| | |
|---|---|
| C07K 14/00 | (2006.01) |
| C07K 5/00 | (2006.01) |
| C07K 16/00 | (2006.01) |
| A61K 39/00 | (2006.01) |
| A61K 39/395 | (2006.01) |
| A61K 49/00 | (2006.01) |
| G01N 33/53 | (2006.01) |

(52) U.S. Cl. ............... 530/350; 530/300; 530/387.1; 424/184.1; 424/130.1; 424/9.2; 436/7.2

(58) Field of Classification Search ............... None
See application file for complete search history.

(56) References Cited

U.S. PATENT DOCUMENTS

| 5,118,606 A | 6/1992 | Lynch et al. |
| 5,536,639 A | 7/1996 | Siman et al. |

FOREIGN PATENT DOCUMENTS

| WO | WO 95/26506 | 10/1995 |

OTHER PUBLICATIONS

Giza et al., "The Neurometabolic Cascade of Concussion," Journal of Athletic Training, 36:228-235, 2001.
Pike, Brian R., et al.: "Accumulation of non-erythroid alphaII-spectrin and calpain-cleaved alphaII-spectrin breakdown products in cerebrospinal fluid after traumatic brain injury in rats", Journal of Neurochemistry, Sep. 2001, pp. 1297-1306, vol. 78, No. 6.
Nath, Rathna, et al.: "Non-erythoid alpha-spectrin breakdown by calpain and interleukin 1beta-converting-enzyme-like protease(s) in apoptic cells: contributory roles of both protease families in neuronal apoptosis", Biochemistry Journal, Nov. 1, 1996, pp. 683-690, vol. 319.
Li, Zhaozhao, et al.: "Peptide alpha-Keto Ester, alpha-Keto Amide, and alpha-Keto Acid Inhibitors of Calpains and Other Cysteine Proteases", Journal of Medicinal Chemistry, Oct. 29, 1993, pp. 3472-3480, vol. 36, No. 22.
Yokota, M., et al.: "Three distinct phases of fodrin proteolysis induced in postischemic hippocampus—involvement of calpain and unidentified protease", Stroke, Oct. 1995, pp. 1901-1907, vol. 26, No. 10.
Nath, Rathna, et al.: "Development and characterization of antibodies specific to caspase-3-produced alpha II-spectrin 120 kDa breakdown product: marker for neuronal apoptosis", Neurochemistry International, 2000, pp. 351-361, vol. 37.
Pike, Brian R., et al.: "Regional calpain and caspase-3 proteolysis of alpha-spectrin after traumatic brain injury", NeuroReport, Aug. 3, 1998, pp. 2437-2442, vol. 9, No. 11.
Zhao, X., et al.: "Maitotoxin Induces Calpain But Not Casepase-3 Activation and Necrotic Cell Death in Primary Septo-Hippocampal Cultures", Neurochemical Research, 1999, pp. 371-382, vol. 24, No. 3.
Pike, Brian R., et al.: "Temporal Relationships Between De Novo Protein Synthesis, Calpain and Calpase 3-like Protease Activation, and DNA Fragmentation During Apoptosis in Septo-Hippocampal Cultures", Journal of Neuroscience Research, 1998, pp. 505-520, vol. 52.
Giza, Christopher C., et al.: "The Neurometabolic Cascade of Concussion", Journal of Athletic Training, Sep. 2001, pp. 228-235, vol. 36, No. 3.
McGinnis, Kim M., et al., "Alterations of Extracellular Calcium Elicit Selective Modes of Cell Death and Protease Activation in SH-SY5Y Human Neuroblastoma Cells", Journal of Neurochemistry, 1999, pp. 1853-1863, vol. 72, No. 5, Lippincott Williams & Wilkins, Inc., Philadelphia, PA.
Nath, Rathna, et al.: "Activation of apoptosis-linked caspase(s) in NMDA-injured brains in neonatal rats", Neurochemistry International, 2000, pp. 119-126, vol. 36.
Bartus, Raymond T., et al. "Time-Related Neuronal Changes Following Middle Cerebral Artery Occlusion: Implications for Therapeutic Intervention and the Role of Calpain," Journal of Cerebral Blood Flow and Metabolism, Nov. 1995, pp. 969-979, vol. 15, No. 6, Lippincott-Raven Publishers, Philadelphia, PA.
Supplementary Partial European Search Report.
Wang, Kevin K.W., et al., "Simultaneous Degradation of αII and βII-Spectrin by Caspase 3 (CPP32) in Apoptotic Cells", The Journal of Biological Chemistry, Aug. 28, 1998, pp. 22490-22497, vol. 273, No. 35, The American Society for Biochemistry and Molecular Biology, Inc., U.S.A.

Primary Examiner—Eileen B. O'Hara
Assistant Examiner—Sandra Wegert
(74) Attorney, Agent, or Firm—Saliwanchik, Lloyd & Saliwanchik

(57) ABSTRACT

Methods for detecting a cell damage relate to the discovery that proteases are selectively activated in subjects suffering from nervous system damage compared to samples from healthy subjects. Breakdown products reflecting activation of proteases that degrade spectrin are produced. A cell injury is detected by providing a biological sample derived from the subject; detecting in the sample the presence of these breakdown products generated by multiple proteases, and correlating the presence of these breakdown products with the presence or type of cell damage.

29 Claims, 7 Drawing Sheets

Patient 1

Patient 2

DETECTION OF SPECTRIN AND SPECTRIN PROTEOLYTIC CLEAVAGE PRODUCTS IN ASSESSING NERVE CELL DAMAGE

CROSS-REFERENCE TO RELATED APPLICATIONS

The present application claims the priority of U.S. provisional patent application No. 60/409,920 entitled "analyzing Central Nervous system Injuries," and filed Sep. 11, 2002.

STATEMENT AS TO FEDERALLY SPONSORED RESEARCH

This invention was made with United States government support under grant numbers DAMD17-99-1-9565 and DAMD17-01-1-0765 awarded by the United States Army, and grant numbers R01 NS39091 and R01 NS40182 awarded by the National Institutes of Health. The United States government may have certain rights in the invention.

FIELD OF THE INVENTION

The invention relates generally to the fields of biology and medicine. More particularly, the invention relates to detecting nerve cell damage in a subject by analyzing a biological sample taken from the subject for protein fragments produced in response to the activation of particular proteases.

BACKGROUND

Brain damage resulting from traumatic, ischemic, and/or chemical etiology is a major health concern worldwide, representing a potentially catastrophic debilitating medical emergency with poor long-term prognosis. For many organ-based diseases, rapid diagnostics for surrogate biomarkers (usually involving blood tests) are invaluable in determining how the disease should be treated. Such tests for assessing traumatic or ischemic brain injury, however, have not been optimized. The most useful diagnostics currently available therefore are computed tomography (CT) and magnetic resonance imaging (MRI). Both of these are expensive, not rapidly accessible in an emergency room environment, and are not useful for diagnosing mild to moderate brain damage. Accordingly, a need exists for improved methods and diagnostic kits for assessing the severity of brain injury. Particularly helpful would be those that provide physicians with quantifiable neurochemical markers to help determine the seriousness of the injury, the anatomical and cellular pathology of the damage, and the implementation of appropriate medical management and treatment.

SUMMARY

The invention relates to the discovery of the accumulation of non-erythroid αII-spectrin and its calpain- and caspase-3-specific breakdown products (SBDPs) in the cerebrospinal fluid (CSF) of human subjects with traumatic brain injury as well as in rodent models of traumatic or ischemic nerve cell injury. The ability to detect and monitor calpain and caspase-3 concurrently after nervous system damage should facilitate (i) determining the presence and/or severity or nerve damage, (ii) selecting the best course of treatment for a subject suspected of having nerve damage, and (iii) analyzing the effectiveness of treatment for nerve damage.

Accordingly, the invention features a method for analyzing nerve cell damage in a subject. The method includes the steps of: (a) providing a biological sample isolated from a subject suspected of having a damaged nerve cell, the biological sample being a fluid in communication with the nervous system of the subject prior to being isolated from the subject (e.g., cerebrospinal fluid, blood, plasma, and serum); (b) detecting in the sample the presence or amount of at least one marker selected from αII spectrin and an αII SBDP generated from proteolytic cleavage of αII spectrin by at least one protease selected from the group consisting of caspase-3 and calpain; and (c) correlating the presence or amount of the marker with the presence or type of nerve cell damage in the subject.

Typically, the subject will be a human patient suspected of having a damaged nerve cell. For example, the method might be applied to a human subject that has sustained trauma (e.g., a blow to the head) or one that presents with symptoms of acute ischemia of a nervous system tissue such as brain (e.g., a patient who appears to have suffered a cerebrovascular accident). The marker(s) being assessed can be one, two, three, four or all of αII spectrin, SBDP150i, SBDP150, SBDP145, or SBDP120.

The step (b) of detecting in the sample the presence or amount of at least one marker selected from αII spectrin and an αII SBDP generated from proteolytic cleavage of αII spectrin by at least one protease selected from the group consisting of caspase-3 and calpain can include contacting the sample or a portion of the sample with an agent (e.g., an antibody) that specifically binds the marker. The agent can be one that does not specifically bind at least one of αII spectrin, SBDP150i, SBDP150, SBDP145, and SBDP120 (i.e., one that binds only a subset of this group); or one that specifically binds only one of αII spectrin, SBDP150i, SBDP150, SBDP145, or SBDP120 (i.e., a mono-specific agent). In some variations of the method of the invention, the step (b) includes immobilizing the biological sample or a portion of the sample on a substrate, and/or contacting the substrate with an agent that specifically binds the marker.

The step (c) of correlating the presence or amount of the marker with the presence or type of cell damage in the subject can include comparing the presence or amount of the marker in the sample with that in a standard sample known to not contain the marker (e.g., a negative control); and/or comparing the presence or amount of the marker in the sample with that in a standard sample known to contain a known amount of the marker (e.g., a positive control or a comparative control for quantifying the amount of the marker in the sample).

In another aspect, the invention features a mixture that includes: (a) a biological sample isolated from a human subject suspected of having a damaged nerve cell, the biological sample being a fluid in communication with the nervous system of the subject prior to being isolated from the subject; and (b) an agent (e.g., an antibody) that specifically binds at least one marker selected from αII spectrin and an αII spectrin breakdown product (SBDP) generated from proteolytic cleavage of αII spectrin by at least one protease selected from the group consisting of caspase-3 and calpain. The marker(s) being assessed can be one or more of αII spectrin, SBDP150i, SBDP150, SBDP145, and SBDP120. The agent can be one that does not specifically at least one of αII spectrin, SBDP150i, SBDP150, SBDP145, and SBDP120; or one that specifically binds only one of αII spectrin, SBDP150i, SBDP150, SBDP145, and SBDP120.

The mixture of the invention can be immobilized on a substrate, e.g., to facilitate detection of the marker(s) in an immunoblot or similar assay. The mixture can further include a detectable label such as one conjugated to the agent, or one conjugated to a substance that specifically binds to the agent (e.g., a detectably labeled secondary antibody).

The invention further includes a kit for analyzing cell damage in a subject. The kit includes: (a) a substrate for holding a biological sample isolated from a human subject suspected of having a damaged nerve cell, the biological sample being a fluid in communication with the nervous system of the subject prior to being isolated from the subject; (b) an agent that specifically binds at least one marker selected from αII spectrin and an αII SBDP generated from proteolytic cleavage of αII spectrin by at least one protease selected from the group consisting of caspase-3 and calpain; and (c) printed instructions for reacting the agent with the biological sample or a portion of the biological sample to detect the presence or amount of the at least one marker in the biological sample.

In the kit, the marker(s) being assessed can be one or more of αII spectrin, SBDP150i, SBDP150, SBDP145, and SBDP120. The agent can be one that does not specifically at least one of αII spectrin, SBDP150i, SBDP150, SBDP145, and SBDP120; or one that specifically binds only one of αII spectrin, SBDP150i, SBDP1150, SBDP145, and SBDP120. The kit can also include a detectable label such as one conjugated to the agent, or one conjugated to a substance that specifically binds to the agent.

As used herein, "bind," "binds," or "interacts with" means that one molecule recognizes and adheres to a particular second molecule in a sample, but does not substantially recognize or adhere to other structurally unrelated molecules in the sample. Generally, a first molecule that "specifically binds" a second molecule has a binding affinity greater than about $10^5$ to $10^6$ moles/liter for that second molecule.

By reference to an "agent that specifically binds" another molecule is meant any substance that binds the other molecule, and displays no substantial binding to other naturally occurring proteins other than those sharing the same antigenic determinants as other molecule. Examples of such agents include antibodies and aptamers.

The term "antibody" includes polyclonal and monoclonal antibodies as well as antibody fragments or portions of immunoglobulin molecules that can specifically bind the same antigen as the intact antibody molecule.

As used herein, a "detectable label" is meant any substance that can be detected either directly or indirectly.

By the phrase "conjugated to" is meant covalently or non-covalently bonded to or otherwise physically associated with.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

DETAILED DESCRIPTION

The invention provides methods, compositions, and kits for detecting and quantifying neurochemical markers to detect nerve cell damage, determine the seriousness of the damage, determine the anatomical and cellular pathology of the damage, and help determine an appropriate treatment for the damage. The invention is based on the characterization of cellular protease (i.e., calpain and caspase-3) activation that occurs in response to nerve cell damage.

Figure 1:
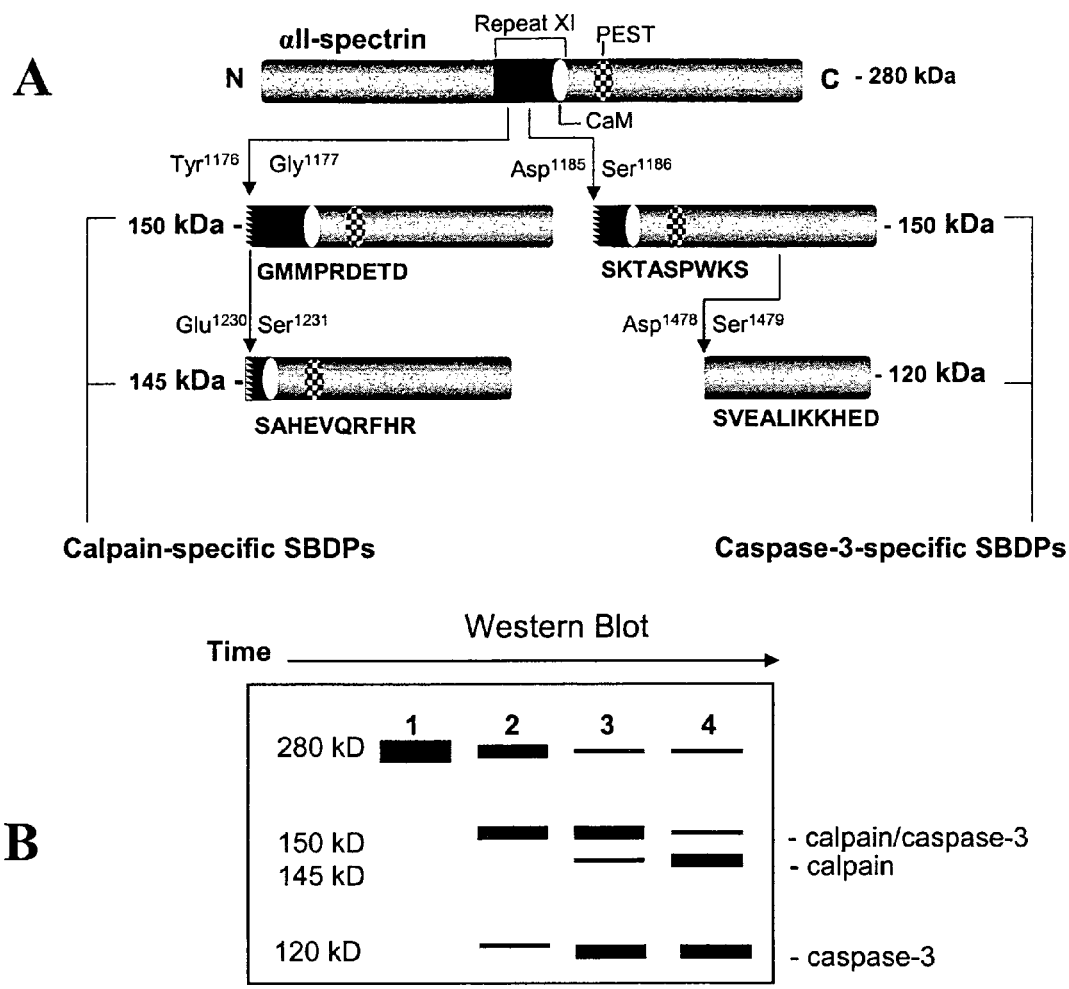
FIG. 1 is two schematic illustrations of (A) calpain and caspase-3 cleavage of non-erythroid αII-spectrin to protease-specific SBDPs, namely calpain-produced 150 kDa fragment (SBDP150) and 145 kDa fragment (SBDP145) and caspase-3 produced 150 kDa fragment (SBDP150i) and 120 kDa fragment (SBDP120) and (B) concurrent detection of full length αII-spectrin and calpain and caspase-3 SBDPs by Western blot analysis.

Through a complex series of signaling events, nerve injury upregulates both calpain and caspase-3-mediated proteolysis of a variety of intracellular substrates including non-erythroid αII-spectrin, a cytoskeletal protein particularly abundant in nerve cells. Referring to FIG. 1A, activated calpain and caspase-3 both bind to αII-spectrin, but cleave it at different sites to yield distinct SBDPs. In particular, calpain initially cleaves αII-spectrin between $Tyr^{1176}$ and $Gly^{1177}$ resulting in the formation of calpain-signature SBDPs of 150 kDa (SBDP150). A second cleavage between $Gly^{1230}$ and $Ser^{1231}$ results in the formation of a second calpain-signature SBDP of 145 kDa (SBDP145). In the same fashion, caspase-3 cleaves αII-spectrin at $Asp^{1185}$ and $Ser^{1186}$ and at $Asp^{1478}$ and $Ser^{1479}$ to yield caspase-3-signature SBDPs of 150 (SBDP150i) and 120 (SBDP120) kDa, respectively. The residues number used are based on human alpha II spectrin (*Homo sapiens*; accession U83867.1, protein number AAB41498). However, as caspase-3 and calpain cleavage sites are fairly conserved among different mammalian species, similar SBDPs are generated in other species in response to nerve cell damage.

Detection and quantification of SBDPs such as SBDP150, SBDP145, SBDP150i, and SBDP120 can therefore be used to detect and characterize nerve cell damage. To illustrate, referring to FIG. 1B, a Western blot can be used to concurrently detect full length αII-spectrin (280 kDa) and calpain- and caspase-3-generated SBDPs. In the absence of calpain or caspase-3 activation, only full length αII-spectrin is detected (lane 1). Activation of caspase-3 only leads to the generation of an additional 150 kDa band and a 120 kDa band (lane 2), whereas activation of calpain only leads to the generation of an additional 150 kDa band and a 145 kDa band. Activation of both caspase-3 and calpain leads to the generation of 4 bands corresponding to the intact 280 kDa αII-spectrin, the 150 kDa fragments, the 145 kDa fragment, and the 120 kDa fragment (lanes 3 and 4). As described below, the two different 150 kDa fragments (i.e., SBDP150 and SBDP150i) can be distinguished from one another, e.g., using an antibody that specifically recognizes the unique N-terminal region each different fragment.

General Biological Methods

Methods involving conventional biological techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Detecting Nerve Cell Damage

Nerve cell damage in a subject is analyzed by (a) providing a biological sample isolated from a subject suspected of having a damaged nerve cell; (b) detecting in the sample the presence or amount of at least one marker selected from αII spectrin and an αII SBDPs generated from proteolytic cleavage of αII spectrin by at least one protease selected from the group consisting of caspase-3 and calpain; and (c) correlating the presence or amount of the marker with the presence or type of nerve cell damage in the subject.

Biological Samples

After insult, nerve cells in in vitro culture or in situ in an animal subject express higher levels of αII spectrin, SBDP150, SBDP145, SBDP150i, and/or SBDP120 than do such cells not subjected to the insult. Thus, samples that contain nerve cells, e.g., a biopsy of a central nervous system or peripheral nervous system tissue are suitable biological samples for use in the invention. In addition to nerve cells, however, other cells express αII-spectrin including, for example, cadiomyocytes, myocytes in skeletal muscles, hepatocytes, kidney cells and cells in testis A biological sample including such cells or fluid secreted from these cells might also be used in an adaptation of the above method to determine and/or characterize an injury to such non-nerve cells.

In addition to increased cell expression, αII spectrin, SBDP150, SBDP145, SBDP150i, and/or SBDP120 also appear in biological fluids in communication with injured cells. Obtaining biological fluids such as cerebrospinal fluid, blood, plasma, serum, saliva and urine, from a subject is typically much less invasive and traumatizing than obtaining a solid tissue biopsy sample. Thus, samples which are biological fluids are preferred for use in the invention. CSF, in particular, is preferred for detecting nerve damage in a subject as it is in immediate contact with the nervous system and is readily obtainable.

A biological sample can be obtained from a subject by conventional techniques. For example, CSF can be obtained by lumbar puncture. Blood can be obtained by venipuncture, while plasma and serum can be obtained by fractionating whole blood according to known methods. Surgical techniques for obtaining solid tissue samples are well known in the art. For example, methods for obtaining a nervous system tissue sample are described in standard neuro-surgery texts such as Atlas of Neurosurgery: Basic Approaches to Cranial and Vascular Procedures, by F. Meyer, Churchill Livingstone, 1999; Stereotactic and Image Directed Surgery of Brain Tumors, 1st ed., by David G. T. Thomas, WB Saunders Co., 1993; and Cranial Microsurgery: Approaches and Techniques, by L. N. Sekhar and E. De Oliveira, 1st ed., Thieme Medical Publishing, 1999. Methods for obtaining and analyzing brain tissue are also described in Belay et al., Arch. Neurol. 58: 1673-1678 (2001); and Seijo et al., J. Clin. Microbiol. 38: 3892-3895 (2000).

Any animal that expresses αII spectrin might be used as a subject from which a biological sample is obtained. The subject can be, e.g., a mammal such as a dog, cat, horse, cow, pig, sheep, goat, chicken, primate, rat, or mouse. Because the experiments presented herein relate to human subjects, a preferred subject for the methods of the invention is a human being. Particularly preferred are subjects suspected of having or at risk for developing traumatic or non-traumatic nervous system injuries, such as victims of brain injury caused by traumatic insults (e.g. gunshots wounds, automobile accidents, sports accidents, shaken baby syndrome), ischemic events (e.g. stroke, cerebral hemorrhage, cardiac arrest), neurodegenerative disorders (such as Alzheimer's, Huntington's, and Parkinson's diseases; Prion-related disease; other forms of dementia), epilepsy, substance abuse (e.g., from amphetamines, Ecstasy/MDMA, or ethanol), and peripheral nervous system pathologies such as diabetic neuropathy, chemotherapy-induced neuropathy and neuropathic pain.

Markers of Calpain and Caspase-3 Activation

The method of the invention features a step of detecting in a biological sample the presence or amount of at least one marker selected from αII spectrin and an αII spectrin breakdown product (SBDP) generated from proteolytic cleavage of αII spectrin by at least one protease selected from the group consisting of caspase-3 and calpain. SBDPs generated from proteolytic cleavage of αII spectrin by caspase-3 include SBDP150i and SBDP120. SBDPs generated from proteolytic cleavage of αII spectrin by calpain include SBDP150 and SBDP145. Depending on the species of animal subject being analyzed, the migration patterns of SBDPs generated from digestion of αII spectrin by caspase-3 and calpain may vary somewhat. Using the methods taught herein, these can be determined empirically.

Detection of αII Spectrin and SBDPs

The invention encompasses methods for detecting the presence of the marker αII spectrin or one of its SBDPs (e.g., SBDP150, SBDP145, SBDP150i, or SBDP120) in a biological sample as well as methods for measuring the level of such marker in a biological sample. An exemplary method for detecting the presence or absence of αII spectrin or one of its SBDPs in a biological sample involves obtaining a biological sample from a subject (e.g., a human patient), contacting the biological sample with a compound or an agent capable of detecting of the marker being analyzed (e.g., an antibody or aptamer), and analyzing binding of the compound or agent to the sample after washing. Those samples having specifically bound compound or agent express of the marker being analyzed.

Methods of the invention can be used to detect αII spectrin or one of its SBDPs in a biological sample in vitro as well as in vivo. The quantity of expression of αII spectrin or one of its SBDPs in a sample may be compared with appropriate controls such as a first sample known to express detectable levels of the marker being analyzed (i.e., a positive control) and a second sample known to not express detectable levels of the marker being analyzed (i.e., a negative control). For example, in vitro techniques for detection of a marker include enzyme linked immunosorbent assays (ELISAs), Western blots, immunoprecipitations and immunofluorescence. Furthermore, in vivo techniques for detection of a marker include introducing a labeled agent that specifically binds the marker into a biological sample or test subject. For example, the agent can be labeled with a radioactive marker whose presence and location in a biological sample or test subject can be detected by standard imaging techniques.

Any suitable molecule that can specifically bind αII spectrin and/or one or more of its SBDPs might be used in the invention. A preferred agent for detecting αII spectrin or one of its SBDPs is an antibody capable of binding to the marker being analyzed, preferably an antibody conjugated with a detectable label. Such antibodies can be polyclonal, or monoclonal. An intact antibody, a fragment thereof (e.g., Fab or F(ab')$_2$), or an engineered variant thereof (e.g., sFv) can also be used. Such antibodies can be of any immunoglobulin class including IgG, IgM, IgE, IgA, IgD and any subclass thereof.

Particularly useful antibodies include those that can distinguish among αII spectrin and/or one or more of its SBDPs. Antibodies that bind only a particular marker or a subset of markers can be made according to known methods. See, Coligan et al, supra. As described below, antibodies that specifically bind one or a subset of αII spectrin SBDPs have been made against the N-terminal ends of individual SBDPs by immunizing animals with peptides corresponding to such N-terminal ends.

Antibody-based assays are preferred for analyzing a biological sample for the presence of αII spectrin and/or one or more of its SBDPs assays. Suitable Western blotting methods are described below in the Examples section. For more rapid analysis (as may be important in emergency medical situations), immunosorbent assays (e.g., ELISA and RIA) and immunoprecipitation assays may be used. See, Coligan et al., supra. As one example, the biological sample or a portion thereof is immobilized on a substrate (e.g., a membrane made of nitrocellulose or PVDF; or a rigid substrate made of polystyrene or other plastic polymer such as a microtiter plate), and the substrate is contacted with an antibody that specifically bind αII spectrin and/or one or more of its SBDPs under conditions that allow binding of antibody to the marker being analyzed. After washing, the presence of the antibody on the substrate indicates that the sample contained the marker being assessed. If the antibody is directly conjugated with a detectable label (e.g., an enzyme, fluorophore, or radioisotope), its presence can be detected by examining the substrate for the detectable label. Alternatively, a detectably labeled secondary antibody that binds the marker-specific antibody can be added to the substrate. The presence of detectable label on the substrate after washing indicates that the sample contained the marker.

Numerous permutations of these basic immunoassays may also be used in the invention. For example, the marker-specific antibody (rather than the biological sample) is immobilized on a substrate, and the substrate is contacted with a marker (e.g., one or more of αII spectrin and/or one or more of its SBDPs) conjugated with a detectable label under conditions that cause binding of antibody to the labeled-marker. The substrate is then contacted with a biological sample under conditions that allow binding of the marker being analyzed to the antibody. A reduction in the amount of detectable label on the substrate after washing indicates that the sample contained the marker.

Although antibodies are preferred for use in the invention because of their extensive characterization, any other suitable agent (e.g., a peptide, an aptamer, or a small organic molecule) that specifically binds αII spectrin and/or one or more of its SBDPs might be used in place of the antibody in the above-described immunoassays. For example, an apatamer that specifically binds αII spectrin and/or one or more of its SBDPs might be used. Apatamers are nucleic acid-based molecules that bind specific ligands. Methods for making aptamers with a particular binding specificity are known. See, e.g., U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

Myriad detectable labels that may be used in a diagnostic assay for marker expression are known in the art. Agents used in methods for detecting αII spectrin and/or one or more of its SBDPs may be conjugated to a detectable label, e.g., an enzyme such as horseradish peroxidase. Agents labeled with horseradish peroxidase can be detected by adding an appropriate substrate that produces a color change in the presence of horseradish peroxidase. Several other detectable labels that may be used are known. Common examples of these include alkaline phosphatase, horseradish peroxidase, fluorescent compounds, luminescent compounds, colloidal gold, magnetic particles, biotin, radioisotopes, and other enzymes.

Correlating Marker Expression with Nerve Cell Damage

The invention employs a step of correlating the presence or amount of αII spectrin and/or one or more of its SBDPs in a biological sample with the severity and/or type of nerve cell (or other αII spectrin-expressing cell) injury. The amount of spectrin and/or its SBDPs in the biological sample directly relates to severity of nerve tissue injury as a more severe injury damages a greater number of nerve cells which in turn causes a larger amount of αII spectrin and/or its SBDPs to accumulate in the biological sample (e.g., CSF). Whether a nerve cell injury triggers an apoptotic and/or necrotic type of cell death can also be determined by examining the SBDPs present in the biological sample. Necrotic cell death preferentially activates calpain, whereas apoptotic cell death preferentially activates caspase-3. Because calpain and caspase-3 SBDPs can be distinguished, measurement of these markers indicates the type of cell damage in the subject. For example, necrosis-induced calpain activation results in the production of SBDP150 and SBDP145; apoptosis-induced caspase-3 activation results in the production of SBDP150i and SBDP120; and activation of both pathways results in the production of all four markers. The results of such a test can help a physician determine whether the administration of calpain and/or caspase inhibitors might be of benefit to a patient. This invention is believed to be the only available approach for concurrent detection of the relative magnitude of apoptotic and necrotic cell death from the same biological sample.

This application may be especially important in detecting age and gender difference in cell death mechanism.

Kits

The invention also provides a kit for analyzing cell damage in a subject. The kit includes: (a) a substrate for holding a biological sample isolated from a human subject suspected of having a damaged nerve cell, the biological sample being a fluid in communication with the nervous system of the subject prior to being isolated from the subject; (b) an agent that specifically binds at least one marker selected from αII spectrin and an αII SBDP generated from proteolytic cleavage of αII spectrin by at least one protease selected from the group consisting of caspase-3 and calpain; and (c) printed instructions for reacting the agent with the biological sample or a portion of the biological sample to detect the presence or amount of the at least one marker in the biological sample.

In the kit, the biological sample can be CSF or blood, and the agent can be an antibody, aptamer, or other molecule that specifically binds at least one of αII spectrin, SBDP150i, SBDP150, SBDP145, and SBDP120. Suitable agents are described above. The kit can also include a detectable label such as one conjugated to the agent, or one conjugated to a substance that specifically binds to the agent (e.g., a secondary antibody).

EXAMPLES

The following examples serve to illustrate the invention without limiting it thereby. It will be understood that variations and modifications can be made without departing from the spirit and scope of the invention.

Example 1

Materials and Methods

Abbreviations: AEBSF, 4-(2-aminoethyl)-benzenesulfonylflouride; EDTA, ethylenediaminetetraacetic acid; EGTA, ethylenebis(oxyethylenenitrilo)tetra acetic acid; DMEM, Dulbecco's modified Eagle's medium; BSA, bovine serum albumin; DPBS, Dulbecco's phosphate buffered saline; DTT, dithiothreitol; FDA, fluorescein diacetate; GFAP, glial fibrillary acid protein; HBSS, Hanks' balanced salt solution; MAP-2, microtubule associated protein-2; PI, propidium iodide; PMSF, phenylmethylsulfonyl fluoride; SDS, sodium dedocyl sulfate; TEMED, N,N,N',N'-tetramethyletheylenediamine; CalpInh-II, calpain inhibitor II (N-acetyl-Leu-Leu-methioninal); Z-D-DCB, pan-caspase inhibitor(carbobenzoxy-Asp-$CH_2$—OC (O)-2-6-dichlorobenzene); PBS, phosphate buffered saline; TLCK, Nα-p-tosyl-L-Lysine chloro methyl; TPCK, N-tosyl-L-phenylalanine chloromethyl ketone.

Cell Culture Techniques

Septo-hippocampal cultures. Eighteen day old rat fetuses were removed from deeply anesthetized dams. Septi and hippocampi were dissected in a dissection buffer (HBSS, with 4.2 mM bicarbonate, 1 mM pyruvate, 20 mM HEPES, 3 mg/ml BSA, pH 7.25). After rinsing in DMEM-DM, tissue was dissociated by trituration through the narrow pore of a flame-constricted Pasteur pipette. Dissociated cells were resuspended in DMEM with 10% fetal calf serum (DMEM-10S) and plated on 24-well poly-L-lysine coated plastic culture plates or 12 mm of German glass (Erie Scientific Co.) at a density of $4.36 \times 10^5$ cells/mL. Cultures were maintained in a humidified incubator in an atmosphere of 5% $CO_2$ at 37° C. After 5 days of culture, the media was changed to DMEM-DM. Withdrawal of fetal calf serum on day 5 did not increase cell death over the next 8 days. Subsequent media changes were carried out three times a week. By day 10 in vitro, astrocytes formed a confluent monolayer beneath morphologically mature neurons.

Pharmacological treatment of septo-hippocampal cells with maitotoxin. Ten day old septo-hippocampal cultures were challenged with 0.01-2.0 nM of maitotoxin (Wako Products, Richmond, Va., Cat.# 131-10731) in DMEM-DM and cell viability was monitored at various post-injury time points. Cultures were exposed to maitotoxin for the entire duration of each experiment. Following maitotoxin challenge, cells were fixed for staining, or protein or DNA extraction was performed.

Treatment of septo-hippocampal cultures with calpain, caspase, and protein synthesis inhibitors. Sister cultures were pretreated with either 37.5 μM calpain inhibitor-II (CalpInh-II) (Boehringer Mannheim), 30 μM of the pan-caspase inhibitor Z-D-DCB (obtained from Biochem), or 1 μg/mL of the protein synthesis inhibitor, cycloheximide (Sigma), 1 hour prior to maitotoxin challenge. The inhibitor concentrations provide optimal inhibition of calpains, caspase-3 (CPP32) proteases, and protein synthesis. In addition, other experiments have confirmed that these doses of CalpInh-II and Z-D-DCB could antagonize calpain and caspase-3 activation accompanying staurosporine-induced apoptosis in septo-hippocampal cultures. This investigation also employed degradation of αII-spectrin to provide independent confirmation that the concentrations of CalpInh-II and Z-D-DCB used in this study to inhibit calpains and caspase-3 proteases. Moreover, 1 μg/mL of cycloheximide blocked calpain and caspase activation as well as apoptotic cell death in this system. Following each experiment, cells were fixed for staining, or protein or DNA extraction was performed.

Treatment of cultures with staurosporine. Ten day old septo-hippocampal cultures were challenged with 0.05-2.0 μM of staurosporine (Calbiochem, La Jolla, Calif., Cat. # 569397) in DMEM-DM and cell viability was monitored at various post-injury time points. Staurosporine was added directly to the media for the entire duration of experiments. Following staurosporine challenge, cells were fixed for staining, or protein or DNA extraction was performed.

Morphological Assessment of Cell Damage

Fluorescein diacetate and propidium iodide assay of cell viability. Fluorescein diacetate (FDA) and propidium iodide (PI) dyes were used to assess cell viability after maitotoxin incubation. FDA enters normal cells and emits a green fluorescence when it is cleaved by esterases. Once cleaved, FDA can no longer permeate cell membranes. Propidium iodide is an intravital dye that is normally excluded from cells. After injury, PI penetrates cells and binds to DNA in the nucleus and emits a red fluorescence. A stock solution of FDA (20 mg/ml) was dissolved in acetone. A PI stock solution was prepared by dissolving 5 mg/mL in PBS. The FDA and PI working solutions were freshly prepared by adding 10 μL of the FDA and 3 μL of PI stock to 10 mL of phosphate buffered saline (PBS). Two-hundred microliters per well of FDA/PI working solution were added directly to the cells. The cells were stained for 3 minutes at room temperature and put on ice. Stained cells were examined with a fluorescence microscope equipped with epi-illumination, band pass 450-490 nM exciter filter, 510 nm chromatic beam splitter, and a long pass 520 nm barrier filter. This filter combination permitted both green and red fluorescing cells to be seen simultaneously.

The percent of viable cells in control cultures and following maitotoxin insult (with or without protease and protein synthesis inhibitors) at different time points was determined from three separate experiments using FDA/PI. The cell viability can be determined since this procedure results in the nuclei of dead cells fluorescing red while the cytoplasm of living cells fluoresces green. Cell loss was calculated in 100× fields (five sequential 100× fields were counted and averaged per well) for three wells in each experiment as a percent of total cell number.

Hoechst staining of apoptotic nuclei. The A-T base-pair-specific dye, Hoechst 33258 (bis-benzimide; Sigma) was used to stain cell nuclei. Following overnight fixation in 4% paraformaldyhide at 4° C., cells grown on German Glass were washed three times with PBS and labeled with 1 µg/mL of the DNA dye Hoechst 33258 in PBS for 5-10 minutes at room temperature, using enough solution to cover the cells completely. The cells were rinsed twice with PBS and then mounted with crystal-mount medium (Biomeda). Cells were observed and photographed on a phase contrast and fluorescence microscope with a UV2A filter.

DNA fragmentation assay. Cells were collected in the same manner as for immunoblotting. Cells in each treatment condition were collected by centrifugation and fixed in suspension in 70% cold ethanol and stored in fixative at −20° C. (24-72 hours). Cells were then centrifuged at 800 g for 5 min. and ethanol was thoroughly removed. Cell pellets were resuspended in 40 µL of phosphate-citrate (PC) buffer consisting of 192 parts of 0.2 M $Na_2HPO_4$ and 8 parts of 0.1 M citric acid (pH 7.8) at room temperature for 1 hour. After centrifugation at 1000 g for 5 minutes, the supernatant was transferred to new tubes and concentrated by vacuum in a SpeedVac concentrator for 15-30 minutes. Three µL of 0.25% Nonidet NP-40 in distilled water was then added, followed by 3 µL of a solution of DNase-free RNase (1 mg/mL). After 30 min. incubation at 37° C., 3 µL of a solution of proteinase K (1 mg/mL) was added and the extract was incubated for additional 30 min. at 37° C. After the incubation, 1 µL of 6× loading buffer (0.25% bromophenol blue, 0.25% xylene cyanol FF, 30% glycerol in water) was added and the entire content of the tube was transferred to a 1.5% agarose gel and electrophoresis was performed in 1× TBE (0.1 M Tris, 0.09 M boric Acid, 1 mM EDTA, pH 8.4) at 40V for 2 hours. The DNA in the gels was visualized and photographed under UV light after staining with 5 µg/mL of ethidium bromide.

Assessing αII-spectrin Degradation

SDS-Polyacrylamide Gel electrophoresis and immunoblotting. At the end of an experiment, cells were harvested from 5 identical culture wells and collected in 15 ml centrifuge tubes and centrifuged at 3000 g for 5 min. The medium was removed and the pellet cells were rinsed with 1× DPBS. Cells were lysed in ice cold homogenization buffer [20 mM PIPES (pH 7.6), 1 mM EDTA, 2 mM EGTA, 1 mM DTT, 0.5 mM PMSF, 50 µg/mL Leupeptin, and 10 µg/mL each of AEBSF, aprotinin, pepstatin, TLCK and TPCK] for 30 min., and sheared through a 1.0 mL syringe with a 25 gauge needle 15 times. Protein content in the samples was assayed by the Micro BCA method (Pierce, Rockford, Ill., USA).

For protein electrophoresis, equal amounts of total protein (30 µg) were prepared in two fold loading buffer containing 0.25 M Tris (pH6.8), 0.2 M DTT, 8% SDS, 0.02% bromophenol blue, and 20% glycerol, and heated at 95° C. for 10 min. Samples were resolved in a vertical electrophoresis chamber using a 4% stacking gel over a 7% acrylamide resolving gel for 1 hour at 200V. For immunoblotting, separated proteins were laterally transferred to nitrocellulose membranes (0.45 µM) using a transfer buffer consisting of 0.192 M glycine and 0.025 M Tris (pH 8.3) with 10% methanol at a constant voltage (100 V) for 1 hour at 4° C. Blots were blocked overnight in 5% non-fat milk in 20 mM Tris, 0.15 M NaCl, and 0.005% Tween-20 at 4° C. Coomassie blue and Panceau red (Sigma, St. Louis, Mo.) were used to stain gels and nitrocellulose membranes (respectively) to confirm that equal amounts of protein were loaded in each lane.

Immunoblots were probed as described below with an anti-αII-spectrin monoclonal antibody (Affiniti Research Products, UK; catalogue #: FG 6090, clone AA6) that detects intact αII-spectrin (280 kDa) and 150, 145, and 120 kDa SBDPs. Following incubation with the primary antibody (1:4000) for 2 hours at room temperature, the blots were incubated in peroxidase-conjugated sheep anti-mouse IgG for 1 hour (1:10,000). Enhanced chemiluminescence reagents (ECL, Amersham) were used to visualize the immunolabeling on Hyperfilm (Hyperfilm ECL, Amersham).

Hoechst 33258 staining in glial or neuronal cell types. To determine the effects of maitotoxin on astroglial and neuronal cell types, cultures were labeled immunocytochemically with GFAP (polyclonal, Sigma) for astroglia or were double labeled with MAP-2 (Stemberger) and NeuN (Chemicon) for neurons and then counterstained with the A-T-base-pair-specific dye, Hoechst 33258. Cultures were fixed in 4% paraformaldyhide for 1 hour at 4° C., rinsed, and stored in PBS. The cultures were permeabilized with 0.3% Triton X-100 for 30 min. and blocked with 1% normal horse or goat serum at room temperature for 1 hour, followed by incubation with GFAP (1:1000), MAP-2 (1:1000) and NeuN (1:1000) antibody overnight at 4° C. The cultures were rinsed three times in PBS and incubated in horseradish peroxidase-conjugated goat anti-rabbit IgG (GFAP) or sheep anti-mouse IgG (MAP-2 and NeuN) (Cappel, 1:1000) for one hour. Cultures were rinsed three times in PBS and diaminobenzidine (DAB, Vector) was used to visualize the reaction. Following incubation in DAB, the reaction was stopped in tap water and cultures were counterstained with Hoechst 33258 for 5 min. Following a final wash, cells were mounted and coverslipped with Cytoseal 280 mounting medium (Stephens). Each slide was observed and photographed in the same field using light (for immunolabeled cells) and fluorescence (for Hoechst 33258 labeled cells) microscopy. A phase contrast microscope (Zeiss Axiovert 135) was used to distinguish the glial and neuronal cell layers.

Statistical Analyses

Each assay was performed three times and data were evaluated by analysis of variance (ANOVA) with a post-hoc Tukey test. Values are given as mean±SEM. Differences were considered significant if $p \leq 0.05$.

Surgical Procedures

Controlled cortical impact traumatic brain injury. A cortical impact injury device was used to produce TBI in rodents. Cortical impact TBI results in cortical deformation within the vicinity of the impactor tip associated with contusion, and neuronal and axonal damage that is constrained in the hemisphere ipsilateral to the site of injury. Adult male (280-300 g) Sprague-Dawley rats (Harlan; Indianapolis, Ind.) were initially anesthetized with 4% isoflurane in a carrier gas of 1:1 $O_2/N_2O$ (4 min.) followed by maintenance anesthesia of 2.5% isoflurane in the same carrier gas. Core body temperature was monitored continuously by a rectal thermistor probe and maintained at 37±1° C. by placing an adjustable temperature controlled heating pad beneath the rats. Animals were mounted in a stereotactic frame in a prone position and secured by ear and incisor bars.

A midline cranial incision was made, the soft tissues were reflected, and a unilateral (ipsilateral to site of impact) craniotomy (7 mm diameter) was performed adjacent to the central suture, midway between bregma and lambda. The dura mater was kept intact over the cortex. Brain trauma in rats was produced by impacting the right cortex (ipsilateral cortex) with a 5 mm diameter aluminum impactor tip (housed in a pneumatic cylinder) at a velocity of 3.5 m/s with a 2.0 mm compression and 150 ms dwell time (compression duration). Velocity was controlled by adjusting the pressure (compressed $N_2$) supplied to the pneumatic cylinder. Velocity and dwell time were measured by a linear velocity displacment transducer (Lucas Shaevitz™ model 500 HR; Detroit, Mich.) that produces an analogue signal that was recorded by a storage-trace oscilloscope (BK Precision, model 2522B; Placentia, Calif.). Sham-injured animals underwent identical surgical procedures but did not receive an impact injury. Appropriate pre- and post-injury management was maintained.

Middle Cerebral Artery Occlusion (MCAO). A noninvasive filament method of MCAO occlusion was used. This method eliminates the need to perform a craniectomy, thereby leaving the skull intact for permanent stereotaxic placement of the EEG electrodes. The basic method described by Longa et al. (Stroke, 20:84-91, 1989) and later modified by Britton et al. (Life Sciences, 60:1729-1740, 1997) was used. The basic procedure consists of blocking blood flow into the MCA with an intraluminal 3-0 monofilament nylon sterile suture with rounded tip introduced through an incision in the external carotid artery (ECA).

Under halothane anesthesia (5% halothane via induction chamber followed by 2% halothane via nose cone), the common carotid artery (CCA) was exposed at the level of external and internal carotid artery bifurcation with a midline neck incision. The internal carotid artery (ICA) was followed rostrally to the pterygopalatine branch and the external carotid artery (ECA) was ligated and cut at its lingual and maxillary branches. To prevent bleeding during suture insertion, the CCA and ICA were temporarily clamped with micro-aneurysm clips. A nylon suture was then introduced into the ICA via an incision on the ECA stump (the path of the suture was monitored visually through the vessel wall) and advanced through the carotid canal approximately 20 mm from the carotid bifurcation until it became lodged in the narrowing of the anterior cerebral artery and thus blocked the origin of the MCA. The skin incision was then closed using sterile autoclips. The endovascular suture remained in place for 2 hr at which time the rat was briefly re-anesthetized and the suture filament retracted to allow reperfusion.

For sham MCAO surgeries, the same procedures were followed but the filament was advanced only 10 mm beyond the internal-external carotid bifurcation and left in place until sacrifice. During all surgical procedures animals were maintained at 37.0° C. using a homeothermic heating blanket (Harvard Apparatus, Holliston, Mass.).

Following surgery animals were placed in recovery cages with air temperature maintained at 22° C. During the 2 hr ischemia period and the initial 4 hr post-reperfusion period 75-watt warming lamps were positioned directly over the top of each cage in order assist in maintaining body temperature normothermic throughout the experiment. At the conclusion of each experiment rat brains showing pathological evidence of subarachnoid hemorrhage upon necropsy were excluded from the study. Also, all rats exhibiting convulsant behaviors at any time post MCAO were excluded immediately prior to the 2 hr reperfusion.

Preparation of Cortical Tissue and CSF

CSF and brain cortices were collected from animals at various intervals after sham-injury or TBI. At the appropriate time-points, TBI or sham-injured animals were anesthetized as described above and secured in a stereotactic frame with the head allowed to move freely along the longitudinal axis. The head was flexed so that the external occipital protuberance in the neck was prominent and a dorsal midline incision was made over the cervical vertebrae and occiput. The atlanto-occipital membrane was exposed by blunt dissection and a 25G needle attached to polyethylene tubing was carefully lowered into the cisterna magna. Approximately 0.1 to 0.15 ml of CSF was collected from each rat. Following CSF collection, animals were removed from the stereotactic frame and immediately killed by decapitation.

Ipsilateral and contralateral (to the impact site) cortices were then rapidly dissected, rinsed in ice cold PBS, and snap frozen in liquid nitrogen. Cortices beneath the craniotomies were excised to the level of the white matter and extended ~4 mm laterally and ~7 mm rostrocaudally. CSF samples were centrifuged at 4000 g for 4 min. at 4° C. to clear any contaminating erythrocytes. Cleared CSF and frozen tissue samples were stored at −80° C. until ready for use. Cortices were homogenized in a glass tube with a TEFLON dounce pestle in 15 volumes of an ice-cold triple detergent lysis buffer (20 mM Hepes, 1 mM EDTA, 2 mM EGTA, 150 mM NaCl, 0.1% SDS, 1.0% IGEPAL 40, 0.5% deoxycholic acid, pH 7.5) containing a broad range protease inhibitor cocktail (Roche Molecular Biochemicals, cat. #1-836-145).

CSF samples were obtained with informed consent from human subjects suffering from TBI, and from control patients without TBI, having hydrocephaly.

Immunoblot Analyses of CSF and Cortical Tissues

Protein concentrations of tissue homogenates and CSF were determined by bicinchoninic acid microprotein assays (Pierce Inc., Rockford, Ill.) with albumin standards. Protein balanced samples were prepared for sodium dodecyl sulfate-polyacrylamide gel electrophoresis (SDS-PAGE) in twofold loading buffer containing 0.25 M Tris (pH 6.8), 0.2 M DTT, 8% SDS, 0.02% bromophenol blue, and 20% glycerol in distilled $H_2O$. Samples were heated for 10 min. at 100° C. and centrifuged for 1 min. at 10,000 rpm in a microcentrifuge at ambient temperature. Forty micrograms of protein per lane was routinely resolved by SDS-PAGE on 6.5% Tris/glycine gels for 1 hour at 200V. Following electrophoresis, separated proteins were laterally transferred to polyvinylidene fluoride (PVDF) membranes in a transfer buffer containing 0.192 M glycine and 0.025 M Tris (pH 8.3) with 10% methanol at a constant voltage of 100 V for 1 hour at 4° C. Blots were blocked for 1 hour at ambient temperature in 5% nonfat milk in TBS and 0.05% Tween-20. Panceau Red (Sigma, St. Louis, Mo.) was used to stain membranes to confirm successful transfer of protein and to insure that an equal amount of protein was loaded in each lane.

Antibodies and Immunolabeling

Immunoblots containing brain or CSF protein were probed with an anti-α-spectrin (fodrin) monoclonal antibody (FG 6090 Ab; clone AA6; cat. # FG 6090; Affiniti Research Products Limited, UK) that detects intact non-erythroid αII-spectrin (280 kDa) and 150, 145, and 120 kDa cleavage fragments to αII-spectrin. To further confirm the specificity of calpain-cleaved spectrin in CSF after TBI, a second antibody (anti-SBDP150; rabbit polyclonal) that recognizes only the calpain-cleaved N-terminal region (GMMPR) of the 150 kDa αII-spectrin breakdown product (SBDP) was also used (Nath et al., 1996b; Saido et al., 1993). Some immunoblots were immunolabeled with an antibody that recognizes erythroid αI-spectrin (Cat.# BYA10881; Accurate Chemical & Scientific Corp., Westbury, N.Y.). Following an overnight incubation at 4° C. with the primary antibodies (FG 6090 Ab, 1:4000 for brain tissue and 1:2000 for CSF; SBDP150 Ab, 1:1000; BYA10881, 1:400), blots were incubated for 1 hour at ambient temperature in 3% nonfat milk that contained a horseradish peroxidase-conjugated goat anti-mouse IgG (1:10,000 dilution) or goat-anti-rabbit IgG (1:3000). Enhanced chemiluminescence (ECL, Amersham) reagents were used to visualize immunolabeling on Kodak Biomax ML chemiluminescent film.

Statistical analyses. Semi-quantitative evaluation of protein levels detected by immunblotting was performed by computer-assisted densitometric scanning (Alphalmager 2000 Digital Imaging System, San Leandro, Calif.). Data were acquired as integrated densitometric values and transformed to percentages of the densitometric levels obtained on scans from sham-injured animals visualized on the same blot. Data was evaluated by least squares linear regression followed by ANOVA. All values are given as mean±SEM. Differences were considered significant if $p<0.05$.

Example 2

Figure 2:
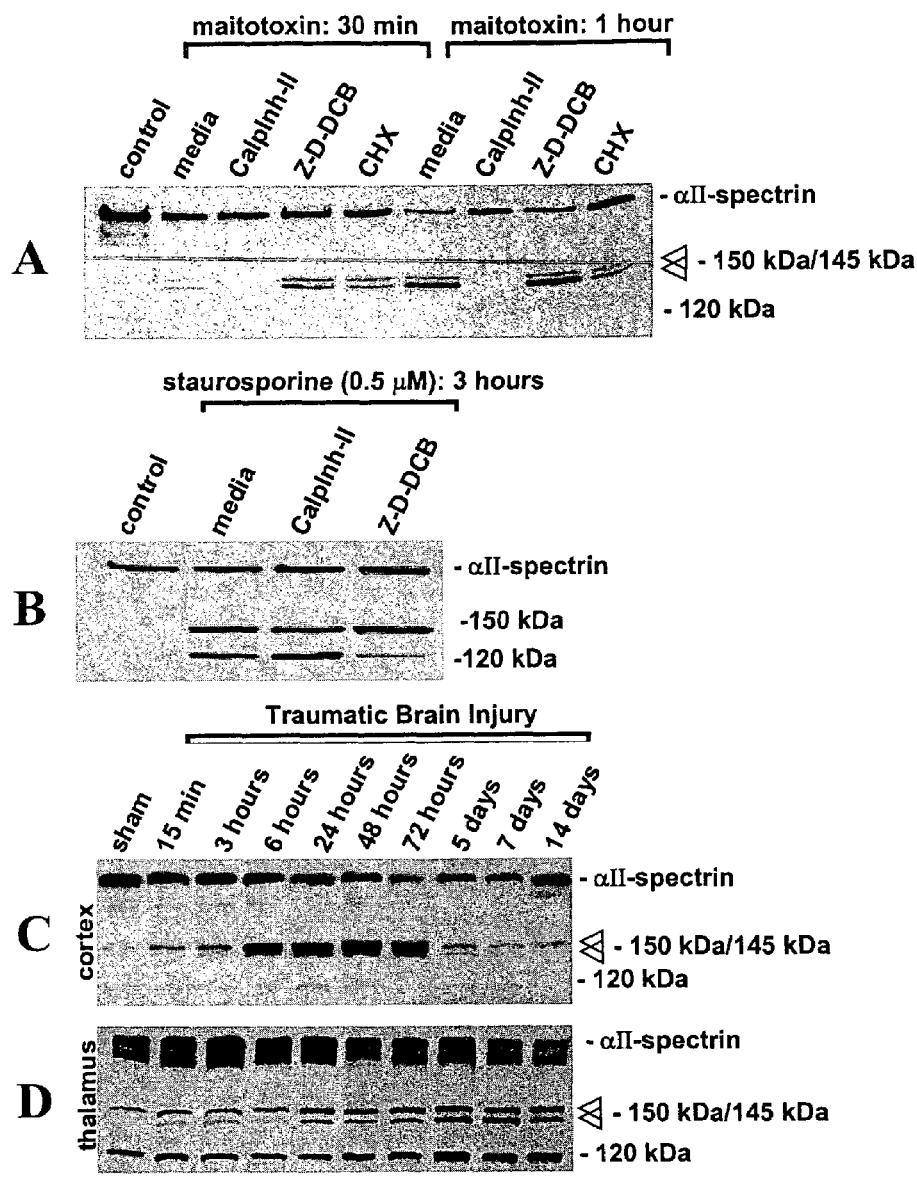
FIG. 2 is four Western blots demonstrating independent or concurrent detection of calpain and caspase-3 SBDPs after different types of injury to cultured neurons (A,B) or brain (C,D).

Detection of Calpain and Caspase-3 SBDPs Following In Vitro and In Vivo Neuronal Insult To investigate the appearance of SBDPs following neuronal insult, septo-hippocampal cultures were prepared as described above and treated with either maitotoxin (30 min, 1 hr) or staurosporine (3 hr). Following harvest and preparation of cell lysates, proteins were separated by SDS-PAGE, transferred onto nylon membranes and immunoblotted using anti-α-spectrin (fodrin) monoclonal antibody (FG 6090) as described above. FIGS. 2A and 2B are representative Western blots demonstrating independent or concurrent detection of calpain and caspase-3 after the different types of injury to cultured neurons. Neuronal cultures exposed to maitotoxin died by necrotic cell death mediated by calpain (145 kDa SBDP) but not caspase-3 (120 kDa SBDP). By contrast, neuronal cultures exposed to staurosporine died by apoptotic cell death mediated by caspase-3 (120 kDa SBDP) but not by calpain (145 kDa SBDP).

In studies performed in vivo, TBI in rat brain was shown to result in activation of calpain only (FIG. 2C) or calpain and caspase-3 (FIG. 2D) depending on the time after injury and brain region being studied. In a comparison of the responses of the cortex and thalamus to TBI, the calpain (145 kDa) SBDP was detectable between 6 and 72 hours after TBI, and was not observable 5-14 days thereafter. In the thalamus from the same animals, both the calpain- and caspase-3 SBDPs were detectable from 15 minutes after TBI up until 14 days post-TBI.

Example 3

Differentiation of SBDP150i, SBDP120, SBDP150, and SABDP145

Figure 3:
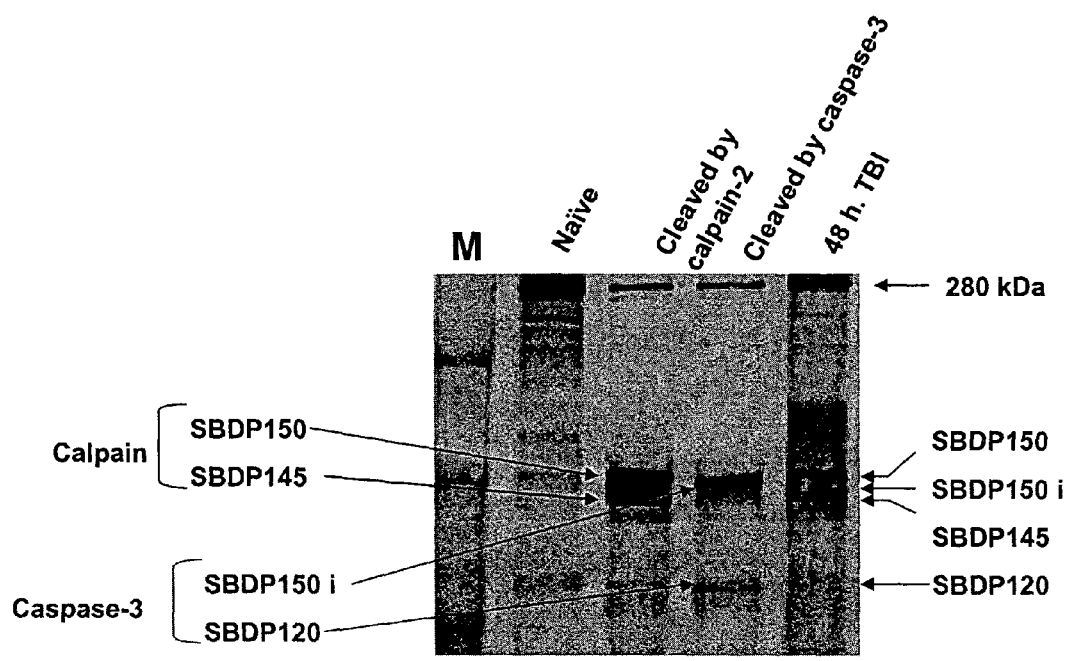
FIG. 3 is a Western blot showing that SBDP150i and SBDP120 can be readily resolved from the SBDP150 and SBDP145.
Figure 4:
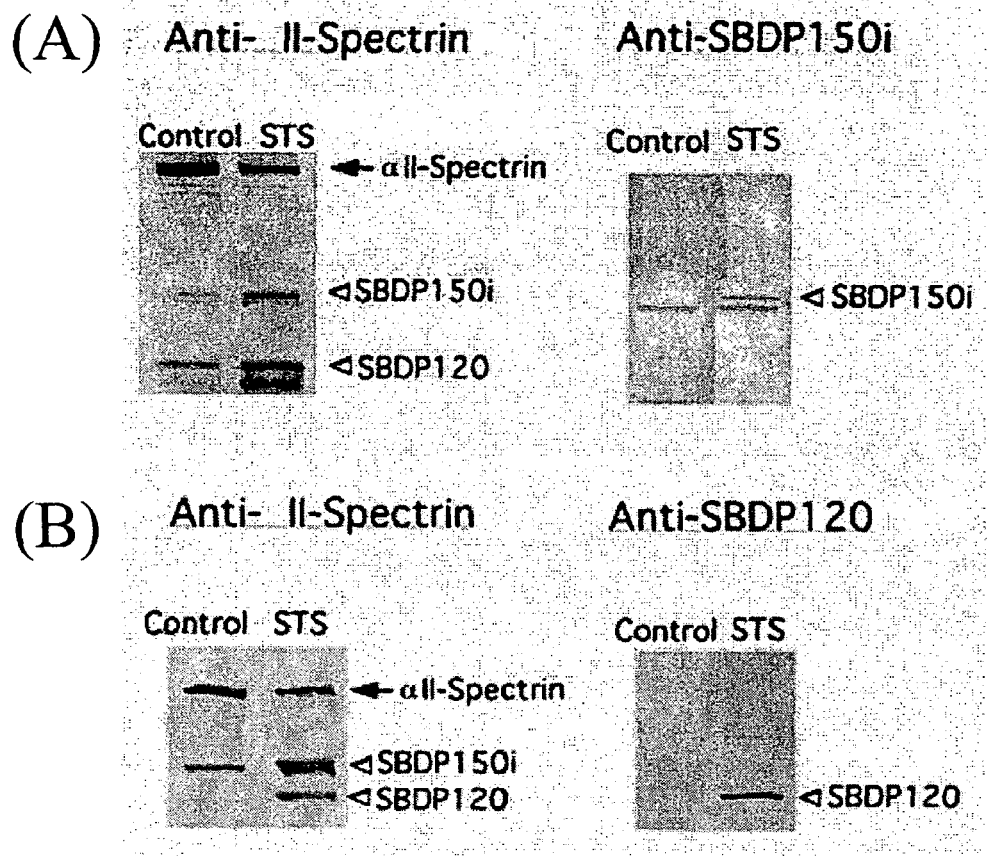
FIG. 4 is four Western blots performed using antibodies specific for SBDP150i and SBDP120.

Referring to FIG. 3, naïve rat brain cortex lysate was either untreated (lane 2 from left) or digested in vitro with purified porcine calpain-2 for 30 min (at a total protein to protease ratio of 1/200) at room temperature (lane 3 from left) or with purified recombinant human caspase-3 (at a total protein to protease ratio of 1/50) for 2 hour at room temperature (lane 4 from left). The αII-spectrin fragmentation patterns are compared to that generated in vivo in the rat hippocampus after TBI ((lane 5 from left). M indicates lane with molecular markers. All samples were run on 8% SDS-polyacrylamide gel electrophoresis and proteins electrotransfered to blotting membrane before exposure to anti-αII-spectrin antibody (Affiniti). SBDP120 and SBDP145 were readily identifiable due to their distinct positions. Caspase-3-produced SBP150i had a slightly higher mobility in the gel and therefore lower position on the blot than did calpain-produced SBDP150 (FIG. 4). Thus, all four SBDPs could be differentiated from one another by Western blot.

Example 4

Western Blots using Antibodies that Specifically Bind SBDP150i and SBDP120

Alpha II spectrin contains four sites at which calpain or capsase-3 act: between $Tyr^{1176}$ and $Gly^{1177}$, between $Gly^{1230}$ and $Ser^{1231}$, between $Asp^{1185}$ and $Ser^{1186}$ and between $Asp^{1478}$ and $Ser^{1479}$. Cleavage at each site generates fragments having a new N-terminal and a new C-terminal, i.e., $NH_2$—$G^{1177}$MMPRDET (SEQ ID NO:1) for SBDP150, $NH_2$—$S^{1186}$AHEVQRF (SEQ ID NO:2), SBDP145, $NH_2$—$S^{1231}$KTASPWK (SEQ ID NO:3) for SBDP150i and $NH_2$—$S^{1479}$VEALIKK (SEQ ID NO:4). Each of these peptides sequences (or related sequences) can be used to generate fragment-specific antibodies. In this example, referring to FIG. 4, SBDP150i and SBDP120-specific antibodies were made using chemically synthesized peptides (i.e., $NH_2$—SKTASPWKC-OH [SEQ ID NO:5] and $NH_2$—SVEALIKKC-OH [SEQ ID NO:7) corresponding to the N-termini of SBDP150i and SBDP120. The last cysteine residue (C) was added to facilitate subsequent coupling to Imject Maleimide-Activated Carrier Protein (keyhole limpet hemocyanin (KLH) (Pierce). The KLH-peptide conjugates (1-2 mg) were then injected over 3-5 months into rabbits to raise polyclonal antibodies. The antibodies are subsequently affinity-purified using protein A Sepharose. The antibodies so produced were used as probes in a Western blotting analysis of human neuroblastoma SH-SY5Y cells that were either untreated (Control) or subjected to staurosporine (STS, 0.5 uM) for 16 h to induce apoptosis. Probing with anti-total spectrin antibody (Affiniti) (A and B, left panels) detected intact aII-spectrin (280 kDa), SBDP150i, and SBDP120. Probing with fragment-specific antibodies detected only the corresponding fragments. Anti-SBDP150 antibody detected only SBDP150i (A, right panel), and anti-SBDP120 antibody detected only the SBDP120 fragment.

Example 5

Detection of Calpain and Caspase-3 SBDPs in CSF of Rodents Following TBI

Figure 5:
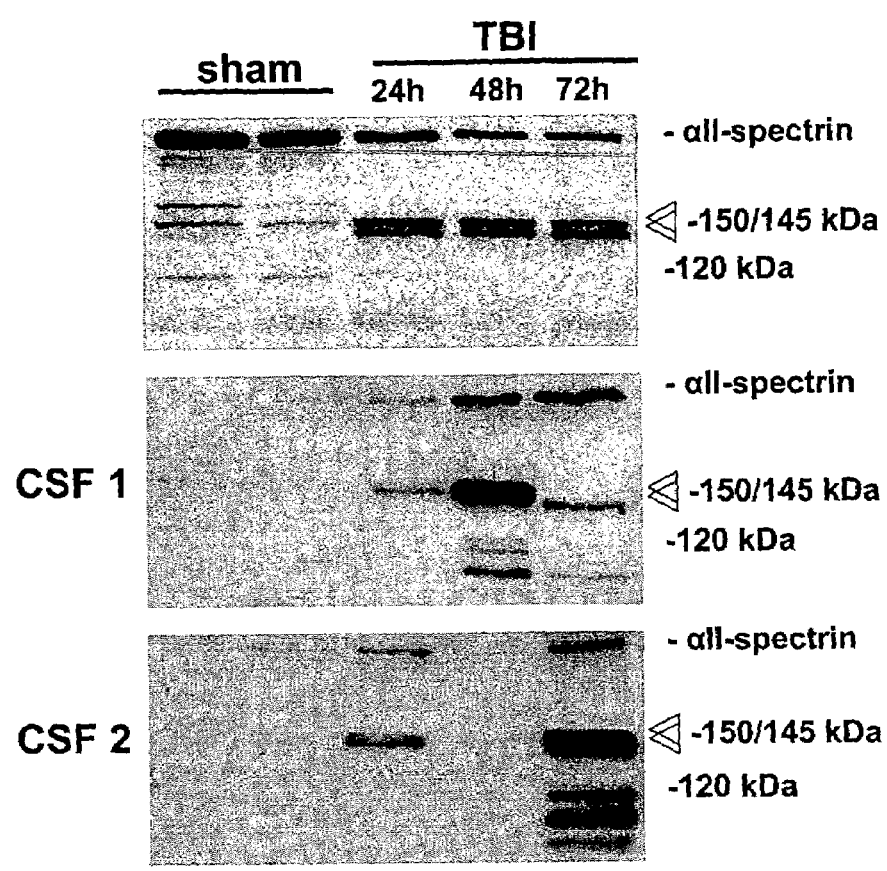
FIG. 5 is three Western blots showing accumulation of αII-spectrin, SBDP145, SBDP120 in the CSF of rodents after TBI.

TBI was induced in rodents as described above. Following TBI or sham operation, samples of CSF were collected and analyzed for presence of calpain-specific and caspase-3-specific SBDPs. Results, shown in FIG. 5, demonstrated independent or concurrent accumulation of calpain-specific and caspase-3-specific SBDPs in the CSF of rodents after TBI. No accumulation of the SBPDs was observed in sham-injured controls. Each lane in the blots represents a different animal. CSF1 and CSF2 are from two separate series of animals, shown to illustrate individual animal's responses. The sensitivity of this assay permits detection of inter-animal differences, which is valuable for prediction of outcome.

The results of this study demonstrated that after TBI, calpains and/or caspase-3 cleaved αII-spectrin in the brain to produce protease-specific SBDPs (145 kDa and 120 kDa). The protease-specific SBDPs then accumulated in the CSF in sufficient levels to be easily detectable on Western blots or by other immunoassays such as ELISA.

Example 6

Detection of Calpain and Caspase-3 SBDPs in CSF of Rodents Following MCAO

Figure 6:
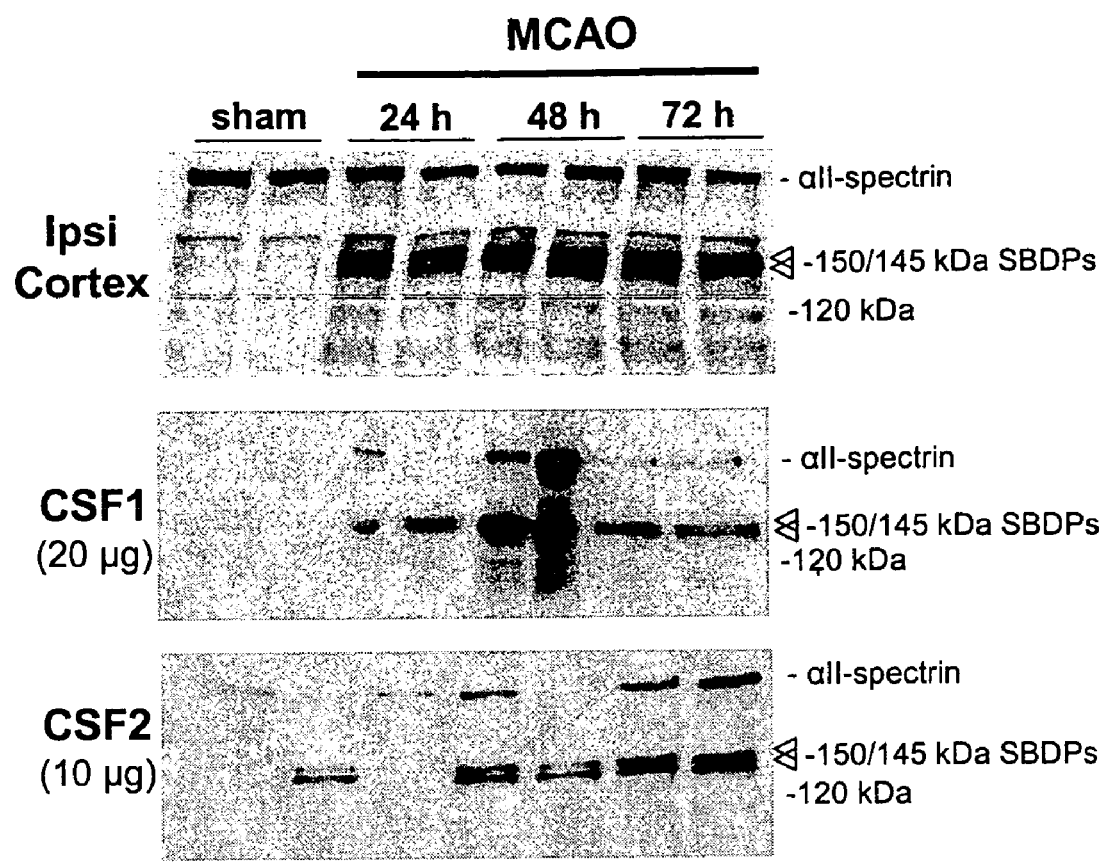
FIG. 6 is three Western blots showing accumulation of αII-spectrin, SBDP145, SBDP120 in CSF of rodents after cerebral ischemia.

The accumulation of calpain-specific and caspase-3-specific SBDPs in CSF was investigated in ischemic injury to rodent brain. MCAO was performed as described above with sham-injured animals serving as controls. Western blotting using the anti-α-spectrin (fodrin) monoclonal antibody (FG 6090) demonstrated independent or concurrent accumulation of calpain-specific and caspase-3-specific SBDPs in CSF in rodents subjected to MCAO but not in sham-injured controls (FIG. 6). Similar to TBI, MCAO caused pronounced accumulation of the calpain-specific 145 kDa SBDP as well as increased accumulation of the caspase-3 specific 120 kDa SBDP. The full length αII-spectrin as well as calpain-specific 145 kDa SBDP and the caspase-3 specific 120 kDa SBDP were easily and robustly detected in rodents subjected to MCAO at 24 to 72 h after the injury, but were not detectable in the sham-injured control rats.

Example 7

Figure 7:
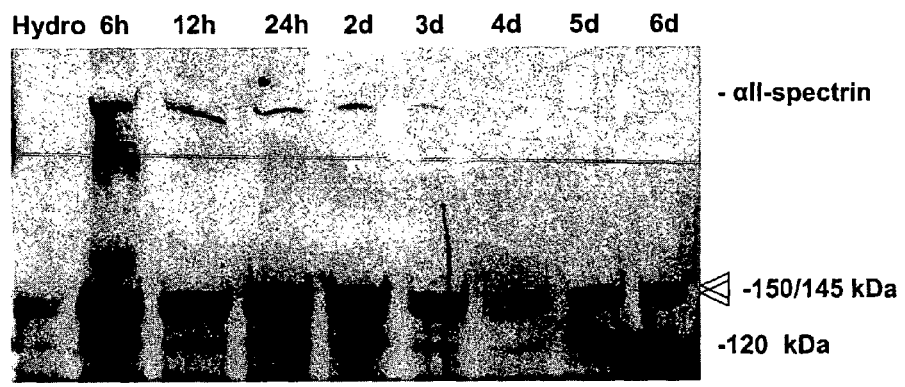
FIG. 7 is two Western blots showing accumulation of αII-spectrin, SBDP145, SBDP120 in CSF of two human patients after severe TBI.
Figure 7:
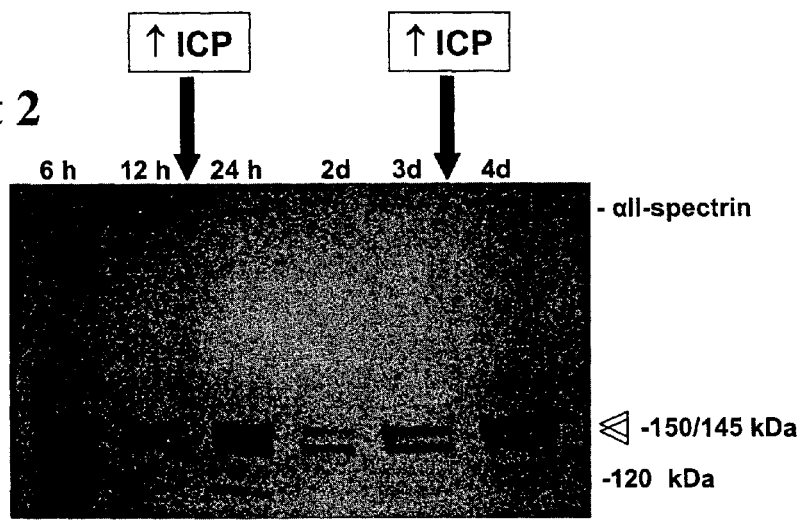

Detection of Calpain and Caspase-3 SBDPs in CSF of Human Patients Following Severe TBI Accumulation of αII-spectrin, calpain-specific 145 kDa, and caspase-3-specific 120 kDa SBDPs was analyzed in samples of human CSF taken at various intervals (12 hr, 24 hr, 2, 3, 4, 5 and 6 days) from two patients who experienced severe TBI. As in the rodent models of TBI and MCAO, the calpain-specific and caspase-3 specific SBDPs were prominent in CSF samples as early as 6 hours after TBI. Levels of SBDPs were much higher in the TBI patient (Patient 1) than in the normal pressure hydrocephalus (Hydro) control patient. (FIG. 7). In Patient 1, the levels of these proteins began to diminish after 2 days post-injury. Calpain and caspase-3 SBDPs were also very prominent within 6 hours of TBI in a second patient that sustained a severe TBI. In Patient 2, the levels of these proteins began to decrease by 12 hours post-injury. However, secondary cerebral injuries caused by increased intracranial pressure (ICP) spikes (arrows) resulted in increased SBDP levels, particularly for the calpain-specific 145 kDa SBDP. These data demonstrated the sensitivity of SBDPs to secondary cerebral injuries as well as the initial insult.

OTHER EMBODIMENTS

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

---

What is claimed is:

1. A mixture comprising:
   a biological sample isolated from a subject suspected of having a damaged nerve cell, the biological sample being a fluid in communication with the nervous system of the subject prior to being isolated from the subject; and
   at least two added antibodies that specifically and independently bind to at least two markers selected from αII-spectrin and an αII-spectrin breakdown product (SBDP) selected from at least one of SBDP150i, SBDP150, SBDP145 and SBDP120 generated from proteolytic cleavage of αII-spectrin by at least one protease selected from the group consisting of caspase-3 and calpain.

2. The mixture of claim 1, wherein the markers consist of αII-spectrin, SBDP150i, SBDP150, SBDP145, and SBDP120.

3. The mixture of claim 1, wherein the at least two antibodies specifically and independently bind to αII-spectrin and at least one of SBDP150i, SBDP150, SBDP145, and SBDP120.

4. The mixture of claim 1, wherein the at least two antibodies specifically and independently bind to SBDP145 and to only one of the group consisting of αII-spectrin, SBDP150i, SBDP150, and SBDP120.

5. The mixture of claim 1, wherein the subject is human.

6. The mixture of claim 1, wherein the SBDP's are immobilized on a substrate.

7. The mixture of claim 1, further comprising a detectable label.

8. The mixture of claim 7, wherein the detectable label is conjugated to the at least two antibodies.

9. The mixture of claim 7, wherein the detectable label is conjugated to a substance that specifically binds to the at least two antibodies.

10. The mixture of claim 1, wherein the antibodies specifically and independently bind to SBDP120, SBDP150i, SBDP145 and optionally to αII-spectrin.

11. The mixture of claim 1, wherein the antibodies specifically and independently bind to SBDP145, SBDP150, SBDP150i and optionally to αII-spectrin.

12. The mixture of claim 1, wherein the antibodies specifically and independently bind to SBDP145, SBDP150i and optionally to αII-spectrin.

13. The mixture of claim 1, wherein the antibodies specifically and independently bind to SBDP145, SBDP150 and optionally to αII-spectrin.

14. The mixture of claim 1, wherein the antibodies specifically and independently bind to SBDP145, SBDP120 and optionally to αII-spectrin.

15. The mixture of claim 1, wherein the antibodies specifically and independently bind to αII-spectrin and SBDP145.

16. The mixture of claim 1, wherein the at least two added antibodies specifically and independently bind only to SBDP145.

17. A kit for analyzing cell damage in a subject, the kit comprising:
   (a) a substrate for holding a biological sample isolated from a human subject suspected of having a damaged nerve cell, the biological sample being a fluid in communication with the nervous system of the subject prior to being isolated from the subject;
   (b) antibodies that specifically and independently bind to at least two markers selected from αII-spectrin and an αII-spectrin breakdown product (SBDP) selected from the group consisting of SBDP120, SBDP145, SBDP150 and SBDP150i wherein the SBDPs are generated from proteolytic cleavage of αII-spectrin by at least one protease selected from the group consisting of caspase-3 and calpain; and
   (c) printed instructions for reacting the antibodies with the biological sample or a portion of the biological sample to detect the presence or amount of the markers in the biological sample.

18. The kit of claim 17, wherein the markers detected are αII-spectrin and an SBDP selected from the group consisting of SBDP150i, SBDP150, SBDP145, and SBDP120.

19. The kit of claim 18, wherein the antibodies detect the presence and amount of αII-spectrin, SBDP150i, SBDP150, SBDP145, and SBDP120.

20. The kit of claim 19, wherein the antibodies specifically detect αII-spectrin, SBDP150, SBDP145, and SBDP120.

21. The kit of claim 17, wherein the subject is a human.

22. The kit of claim 17, further comprising a detectable label.

23. The kit of claim 22, wherein the detectable label is conjugated to at least one antibody.

24. The kit of claim 22, wherein the detectable label is conjugated to a secondary antibody that specifically binds to at least one antibody.

25. A kit for analyzing cell damage in a subject, the kit comprising:
   (a) a substrate for holding a biological sample isolated from a subject suspected of having a damaged nerve cell, the biological sample being a fluid in communication with the nervous system of the subject prior to being isolated from the subject;
   (b) an antibody that specifically and independently binds to a marker identified as αII-spectrin breakdown product (SBDP) 145 kDa generated from proteolytic cleavage of αII-spectrin by at least one protease selected from the group consisting of caspase-3 and calpain; and
   (c) printed instructions for reacting the antibody with the biological sample or a portion of the biological sample to detect the presence or amount of the 145 kDa marker in the biological sample.

26. The kit of claim 25, further comprising one or more antibodies that specifically and independently bind to an SBDP selected from the group consisting of SBDP150i, SBDP150 and SBDP120.

27. The kit of claim 26, further comprising an antibody that specifically and independently binds to αII-spectrin.

28. The kit of claim 25, further comprising an antibody that specifically and independently binds to αII-spectrin.

29. The kit of claim 25, wherein the subject is human.

* * * * *

UNITED STATES PATENT AND TRADEMARK OFFICE
CERTIFICATE OF CORRECTION

| | | |
|---|---|---|
| PATENT NO. | : 7,291,710 B2 | Page 1 of 1 |
| APPLICATION NO. | : 10/660069 | |
| DATED | : November 6, 2007 | |
| INVENTOR(S) | : Ronald L. Hayes, Ka-Wang (Kevin) Wang and Brian R. Pike | |

It is certified that error appears in the above-identified patent and that said Letters Patent is hereby corrected as shown below:

<u>Column 3,</u>
Line 25, "SBDP1150" should read --SBDP150--.

Signed and Sealed this

First Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 7,291,710 B2  Page 1 of 1
APPLICATION NO. : 10/660069
DATED : November 6, 2007
INVENTOR(S) : Ronald L. Hayes, Ka-Wang Kevin Wang and Brian R. Pike It is certified that error appears in the above-identified patent and that said Letters Patent is hereby corrected as shown below:

In the Specification

Column 1,
Lines 20-21, "The United States government may have certain rights in the invention." should read
--The United States government has rights in the invention.--.

Signed and Sealed this
Twelfth Day of August, 2014

Michelle K. Lee
*Deputy Director of the United States Patent and Trademark Office*

SEQUENCE LISTING

```
<160> NUMBER OF SEQ ID NOS: 6

<210> SEQ ID NO 1
<211> LENGTH: 7
<212> TYPE: PRT
<213> ORGANISM: HOMO SAPIENS

<400> SEQUENCE: 1

Met Met Pro Arg Asp Glu Thr
1               5

<210> SEQ ID NO 2
<211> LENGTH: 7
<212> TYPE: PRT
<213> ORGANISM: HOMO SAPIENS

<400> SEQUENCE: 2

Ala His Glu Val Gln Arg Phe
```

```
<210> SEQ ID NO 3
<211> LENGTH: 7
<212> TYPE: PRT
<213> ORGANISM: HOMO SAPIENS

<400> SEQUENCE: 3

Lys Thr Ala Ser Pro Trp Lys
1               5

<210> SEQ ID NO 4
<211> LENGTH: 7
<212> TYPE: PRT
<213> ORGANISM: HOMO SAPIENS

<400> SEQUENCE: 4

Val Glu Ala Leu Ile Lys Lys
1               5

<210> SEQ ID NO 5
<211> LENGTH: 9
<212> TYPE: PRT
<213> ORGANISM: HOMO SAPIENS

<400> SEQUENCE: 5

Ser Lys Thr Ala Ser Pro Trp Lys Cys
1               5

<210> SEQ ID NO 6
<211> LENGTH: 9
<212> TYPE: PRT
<213> ORGANISM: HOMO SAPIENS

<400> SEQUENCE: 6

Ser Val Glu Ala Leu Ile Lys Lys Cys
1               5
```